United States Patent [19]
Felton

[11] Patent Number: 5,998,330
[45] Date of Patent: Dec. 7, 1999

[54] UV STABLE MICROBIAL INSECTICIDES, METHODS OF MAKING, METHODS OF USING

[75] Inventor: Gary W. Felton, Fayetteville, Ark.

[73] Assignee: The Board of Trustees of the University of Arkansas, Little Rock, Ak.

[21] Appl. No.: 08/803,670

[22] Filed: Feb. 21, 1997

Related U.S. Application Data

[60] Provisional application No. 60/013,586, Feb. 23, 1996.

[51] Int. Cl.⁶ .............................. A01N 35/06; C07C 50/00
[52] U.S. Cl. ........................ 504/116; 504/125; 504/123; 504/145; 504/161; 47/58.1; 568/303; 568/308; 424/93.1; 424/93.46; 424/93.461; 424/93.6; 549/552; 252/404; 435/267
[58] Field of Search ................................ 424/93.1, 93.46, 424/93.461, 93.6; 47/58, 58.1; 800/200, DIG. 71, DIG. 44; 435/267; 552/291; 252/404; 549/552; 568/303, 308; 504/116, 125, 123, 145, 161

[56] References Cited

PUBLICATIONS

Felton et al. J. Chem. Ecol. 1990 vol. 16, (4), 1221–1236.

Ludlum et al. J. Chem. Ecol. 1991, vol. 17 (1), 217–237.

*Primary Examiner*—Anthony C. Caputa
*Assistant Examiner*—Khalid Masood
*Attorney, Agent, or Firm*—J. M. (Mark) Gilbreth; Robert W. Strozier; Gilbreth & Strozier, P.C.

[57] ABSTRACT

A method of treating vegetation by application of a microbial insecticide in which a quinone has been covalently bonded to the viral occlusion body surface of the microbial insecticide in order to improve the UV stability of the microbial insecticide by forming a protective shield around the pathogen.

11 Claims, 1 Drawing Sheet

UV STABLE MICROBIAL INSECTICIDES, METHODS OF MAKING, METHODS OF USING

RELATED APPLICATION DATA

This application claims priority from U.S. Provisional application Ser. No. 60/013,586 filed Feb. 23, 1996.

BACKGROUND OF THE INVENTION

1. Field of the Invention

The present invention relates to insecticides, to methods of making insecticides, and to a method of using insecticides. In another aspect, the present invention relates to insecticides having enhanced UV stability, to methods of making insecticides more UV stable, and to a method of using such insecticides. In even another aspect, the present invention relates to microbial insecticides having enhanced UV stability, to methods of making such insecticides, and to a method of using such insecticides. In still another aspect, the present invention relates to microbial insecticides having enhanced UV stability by utilizing a common dietary constituent that is directly bonded to the microbial pathogen, to methods of making such insecticides, and to a method of using such insecticides.

2. Description of the Related Art

Insects can be infected by viruses, bacteria, protozoa, fungi, rickettsiae and nematodes. Some of these disease organisms may be very pathogenic to their hosts and cause a high rate of mortality. During the last several decades it has been successfully demonstrated that insect pathogens can be applied for the temporary control of insect pests. A growing number of commercial products using *Bacillus thuringiensis* (BT) strains, nuclear polyhedrosis viruses (NPV), granulosis viruses, microsporidians, nematodes, and fungi have been developed. The high specificity and low environmental impact of these pathogens have made them particularly attractive components for insect pest management. With the advent of genetic engineering, it has become routine to express novel insecticidal proteins in some of these pathogens, particularly the baculoviruses. The toxins from BT have also been expressed directly in crop plants, but molecular techniques are also being utilized to enhance the toxicity and host range of various BT isolates to use as spray treatments. These developments assure that the market will see an increasing number of genetically modified microbial pesticides that offer safer alternative to synthetic pesticides.

However, several environmental factors may limit the persistence and efficacy of these agents. The foremost destructive factor limiting their performance in the field is sunlight. Ultraviolet radiation is known to rapidly inactivate viruses, bacteria, mirosporidians, and fungi within hours to days. Consequently, considerable research effort has taken place to increase the persistence of the pathogens for as long as possible.

The most commonly attempted method to enhance UV-stability in the field for BT and NPV has been to use spray formulations containing sunlight screens. A host of materials have been tested for improving sunlight persistence. These compounds can be classified as those that reflect UV and those that absorb UV light. The following tables list some of the compounds that have been tested and in some cases, obtained patents for UV protection of NPV and/or BT:

TABLE 1

UV Reflectants Used for Protecting Microbial Pesticides

| Protectant | Protectant | Concentrations used | Source |
|---|---|---|---|
| aluminum oxide | $AlO_2$ | 50:1 Al:NPV | |
| aluminum powder | Al | | |
| Blancophor SV ® | $TiO_2$ | | Chemical Developments of Canada |
| Tinopal CBS ® | stilbene derivative | | Ciba Geigy, Co. |
| Tinopal RBS200 ® | stilbene derivative | | Ciba Geigy, Co. |

TABLE 2

UV Absorbants

| Protectant | Composition | Concentrations used | Source |
|---|---|---|---|
| Amelozan ®) | | 0.05% | Hoechst Chemical Co. FDR |
| benzyl cinnamate | | 3% | |
| carbon | india ink, activated carbon, etc. | 1 kg/ha | Activated Carbon Co. Pittsburg, PA 15230 |
| Chevron ® | | 2.0% | Chevron Chemical Co. USA. |
| lignin sulphate | natural phenolic polymer | 8.5% | |
| soy hydrosylate | | 3% | |
| yeast | | 5% | |
| milk | | 3% | |
| Egg albumin | | 3% | Nutritional Biochemicals Corp. USA |
| NuFilm 17 ® | | | |
| SAN-240 wp(75) ® | | | Sandoz Inc. Homestead, Fl |
| Shade IMC 90001 ® | flavonoids (probably quercetin) | 0.25 to 6.0% | Sandoz Inc. Homestead, Fl |
| Unival DS49 ® | | 1.0% | |

Several factors limit the use of these protectants. First high application rates of most of the compounds are not cost effective. Tank mixes requiring up to 8% of any of the additives becomes cost prohibitive. Also, high usage rates of reflectant compounds may severely disrupt photosynthesis on leaf surfaces. Some compounds such as the aluminum derivatives and stilbenes may be relatively toxic and thus should not be used. Shade® (presumably a flavonoid plant product) was one of the most widely tested compounds but produced sporadic results and required high concentrations (up to 6%) for effective protection.

Thus there is a need in the art for insecticides, and methods of making insecticides which do not suffer from the disadvantages of the prior art.

There is another need in the art for insecticides with enhanced UV stability.

There is even another need in the art for insecticides with reduced toxicity.

There is still another need in the art for insecticides with reduces application rates.

SUMMARY OF THE INVENTION

It is an object of the present invention to provide a method for covalently bonding quinones to microbial insecticides.

It is another object of the present invention to provide a microbial insecticide with enhanced UV stability and a method for making and using same.

It is even another object of the present invention to provide a microbial insecticides with reduced toxicity and a method for making and using same.

It is still another object of the present invention to provide a microbial insecticides with reduces application rates and a method for making as using same.

These and other objects of the present invention will become apparent to those of skill in the art upon review of this specification, including its drawings and claims.

According to one embodiment of the present invention there is provided a method of treating vegetation with a microbial insecticide to which a quinone has been covalently bonded to the viral occlusion body surface of the mircrobial insecticide.

According to another embodiment of the present invention there is provided a method of making insecticides. The method generally includes covalently binding a quinone to the viral occlusion body surface of a microbial insecticide in order to improve the UV stability of the microbial pesticide.

According to even another ebodiment of the present invention there is provided an insecticide composition of a quinone covalently bound to the viral occlusion body surfaced of the mircrobial insecticide.

These and other embodiments of the present invention will become apparent to those of skill in the art upon review of this specification, including its drawings and claims.

DETAILED DESCRIPTION OF THE INVENTION

Figure 1:
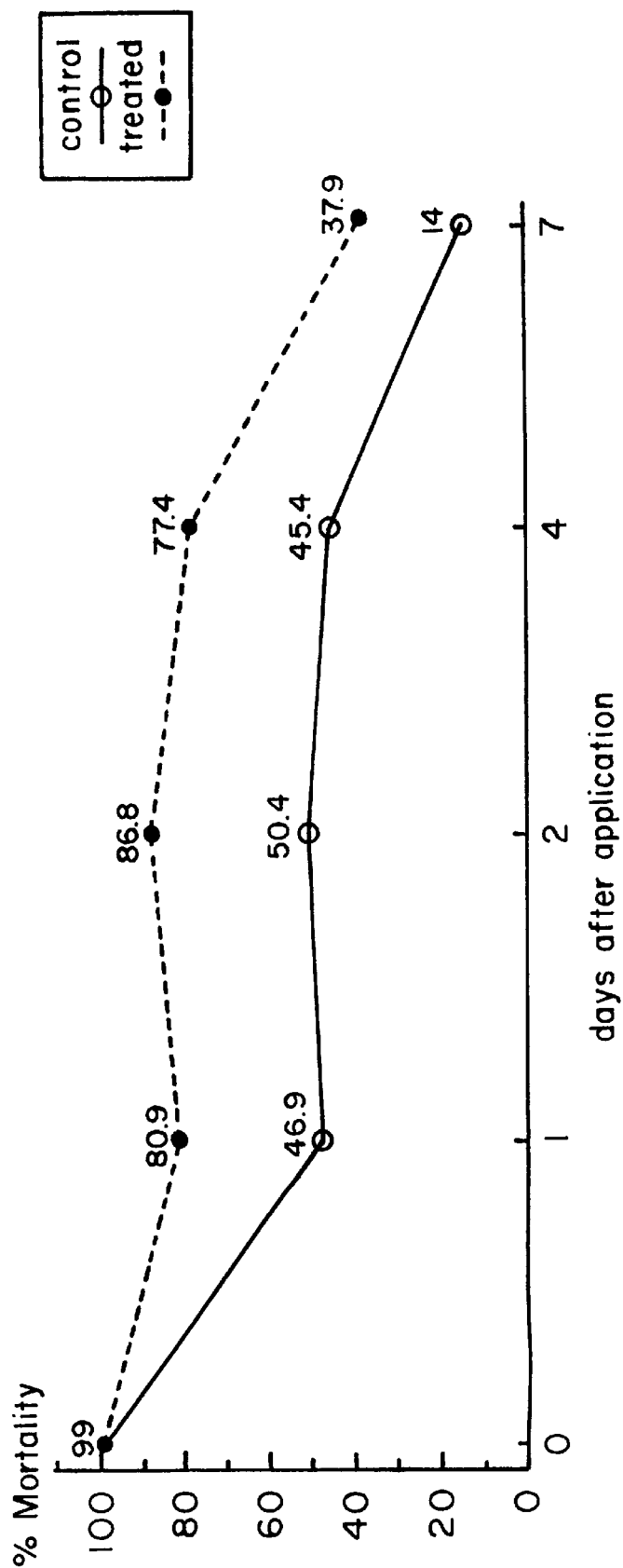
FIG. 1. Is a graph showing the effect of chemical modification of HzSNPV on insecticidal activity following sunlight exposure over a seven day period.

Disclosed in this application is a process for improving the UV-stability of microbial pesticides that is unique in that it utilizes a common dietary constituent that is directly bonded to the pathogen to provide protection. This treatment optimizes UV protection by forming a protective shield surrounding the pathogen. Consequently relatively minute amounts of the chemical is required for successful protection. This minimizes cost as well as mitigating any potential environmental effects.

In the practice of the present invention a microbial insecticide is treated by contacting the microbial insecticide with a quinone, to form a treated microbial composition in which the quinone is covalently bonded to the viral occlusion surface of the microbial insecticide.

The UV stabilizers utilized in the present invention may be any stabilizer that is suitable to covalently bond to the viral occlusion surface of the microbial insecticide and improve the UV stability.

Preferably such stabilizers are quinones that covalently bind to the viral occlusion body surface of the mircrobial insecticide. While the quinone utilized in the present invention may be made by any suitable method, it is preferably made by the oxidation of a phenolic by an enzyme in the presence of a catalyst. Non-limiting examples of suitable phenolics include plant phenolics such as chlorgenic acid, dihydroxyphenylalanine or quebracho tanin. Most preferred are plant phenolics which are also non-toxic dietary constituents, so as not to pose any toxic or nutritional threat.

Additionally, it is desirable that the stabilizer protect against specific UV wavelengths that are damaging to the particular microbial insecticide. For example, the chlorogenic acid molecule absorbs UV very strongly between the wavelengths of 200 and 360 nm. These wavelengths are detrimental to NPV and other entomopathogens such as *Bacillus thuringiensis*.

Non-limiting examples of suitable enzymes include tyrosinase, laccase or peroxidase.

As a specific non-limiting example, the oxidation of chlorogenic acid by tyrosinase produces reactive ortho-quinones that covalently bind to the viral occlusion body surface.

It should be understood that the quinone utilized in the present invention may be made insitu by addition of the phenolic and an oxidation catalyst in the reaction mixture along with the microbial insecticide. As an alternative to the insitu formation of the quinone, the phenolic and catalyst could be reacted separate from and prior to contact with the microbial insecticide.

Non-limiting examples of oxidizing agents for chlorogenic acid include transition metals such as Fe, Cu, Zn, Ni, Co, and for phenolics and chlorogenci acid include transition metals such as Fe and Cu. These metals are very attractive catalysts as: oxidation can be carried out at neutral pH to protect the pathogen; the cost of the catalysts are very minimal; and the concentrations of metals required for catalysis are minuscule (nanomolar range). Also, other less expensive phenolics with similar UV absorbing properties may be as effective or even more effective than chlorogenic acid. For instance, DOPA or dihydroxyphenylalanine will readily bind to nuclear polyhedrosis viruses ("NPV") when oxidized by Fe.

Non-limiting examples of classes of suitable microbial insecticides include *Bacillus thuringiensis* strains, nuclear polyhedrosis viruses, granulosis viruses, microsporidians, bacteria, rickettsias, fungi, protozoa, and combinations thereof. Preferably, the class of microbial insecticides utilized in the present invention are nuclear polyhedrosis viruses.

Non-limiting examples of suitable microbial insecticides include the celery loper virus, gypsy moth NPV, AcMNPV, codling moth granulosis virus, HzSNPV, *Bacillus thuringiensis, Bacillus popillae, Beauvaria bassiana, Metarrhizium anisopliae, Nomuraea releyi, Hirsutella spp, Lagenidium giganteum, Entomophtora*, and *Nosema locustae*. A preferred species of microbial insecticide includes the HZSNPV strain.

In the manufacture of the insecticide of the present invention, the microbial insecticide and a quinone are generally contacted at suitable reaction conditions to covalently bond the quinone, produced from the oxidation of the phenolic compound, to the viral occlusion body surface of the mircrobial insecticide. Again, the quinone may be formed insitu by contacting a phenolic compound, and enzyme and an oxidation catalyst.

The reaction of the microbial insecticide and the quinone must be conducted at a reaction temperature and pressure sufficiently high to provide reaction activity, but not so high as to cause undue degradation of any of the reactants or product. Generally, this means for atmosphereic pressure that the temperature will be in the range of about 5° C. and about 60° C., preferably in the range of about 15° C. and about 35° C., and more preferably in the range of about 25° and 30° C. Suitable temperatures at other pressures may also be utilized.

Generally, the ratio of stabilizer to virus is less than about 50:1, preferably less than about 40:1 more preferably less than about 10:1, and more preferably, less than about 2:1, and most prefereably 1:1 or less. Suitable ranges for the ratio of stabilizer to virus are generally in the range of about 50:1 to about 1:50, preferably in the range of about 40:1 to about 1:40, more preferably in the range of about 10:1 to about 1:10, even more preferably in the range of about 2:1 to about 1:2.

While not necessary, it is generally preferred to utilize an excess of stabilizer so that the probability of treatment of a substantial portion of the microbial insecticide is enhanced. Therefore, suitable ranges of stabilizer to microbial insecticide ratios are generally in the range of about 50:1 to about 1:1, preferably in the range of about 40:1 to about 1:1, more preferably in the range of about 10:1 to about 1:1, and even more preferably in the range of about 2:1 to about 1:1.

In the present invention, the quinone and the microbial insecticide are generally contacted together for a reaction time sufficient to treat at least a portion of, most preferably a sufficient portion of the microbial insecticide in the reaction mixture. Generally this means that the quinone and the microbial insecticide are generally contacted together for a reaction time in the range of about 0.1 seconds to about 72 hours. Preferably, the quinone and the microbial insecticide are generally contacted together for a reaction time in the range of about 1 minute to about 10 hours, more preferably in the range of about 15 minutes to about 3 hours, even more preferably in the range of about 30 minutes to about 2 hours.

The treated microbial insecticide of the present invention is applied to vegetation at rates as are well known in the art for such microbial insecticides. Generally, the treated microbial insecticide of the present invention is applied to vegetation in an amount suitable to effectively treated for a targeted insect, organism or other pest. Generally, the treated microbial insecticide of the present invention is applied to vegetation in an amount in the range of about 0.1 g to about 5 kg per hectare of vegetation. Preferably, the treated microbial insecticide of the present invention is applied to vegetation in an amount in the range of about 1 g to about 1 kg per hectare of vegetation, more preferably in an amount in the range of about 2 g to about 200 g per hectare of vegetation, even more preferably in an amount in the range of about 20 g to about 150 g per hectare of vegetation, still more preferably in an amount in the range of about 40 g to about 60 g per hectare of vegetation.

Non-limiting examples of the types of vegetation that may be treated by the treated microbial insecticide include plants, vegetables, trees, fruit trees, fruit plants, grains, grasses, and fiber plants (such as cotton).

The treated microbial insecticide of the present is generally applied in diluted form utilized an application medium, as is known in the art. For example, common commercially available dilutions of microbial insecticides are on the order of about $6 \times 10^9$ occlusion bodies per gram of application medium.

EXAMPLE

The following example is provided merely to illustrate the present invention, and is not intended to limit the scope of the claims.

Insects

The highly polyphagous agricultural pest, *Helicoverpa zea* was used in this study. The colony was maintained on semisynthetic diet at 28 C. (L:D 12:12).

Treatment and Application of Virus

The nuclear polyhedrosis virus HZSNPV was obtained as a commercial preparation (Elcar) from Sandoz Crop Protection, Des Plaines, Ill. Fifty mg of viral occlusion bodies (OB) were incubated in 20 ml 0.05 M potassium phosphate buffer, pH 7.0, with 50 mg chlorogenic acid and 100 units of tyrosinase (which is polyphenol oxidase—Sigma Chemical Co.) for one hr at 30 C. Controls included treatments lacking both chlorogenic acid and tyrosinase and one with chlorogenic alone.

Application of Virus to Plants and Test for Sunlight Inactivation

Following incubation, the viral suspension was diluted and applied to soybean plants (RO stage) with a boom-type sprayer. Thirty leaves were collected from the canopy of plants on day 0 (immediately after spraying), day 1, day 2, day 4, and day 7. The experiment was replicated four times during September and October of 1994 and 1995.

Bioassay of Viral Activity

A 3-day old 2nd instar larva was placed on a leaf in a 1 oz plastic rearing cup. After 2 days the larva was transferred to the diet and mortality was recorded, Mortality was recorded daily until pupation.

Example Results

The activity of HzSNPV to larvae was unaffected by treatment with chlorogenic acid and/or tyrosinase in the absence of sunlight exposure (data not shown).

The present invention has been illustrated mainly by reference to enhancing the UV stability of viruses. It is to be understood that the present invention finds applicability in enhancing the UV stability of bacteria, protozoa, fungi, rickettsiae and nematodes. Specifically, the present invention is believed to have applicability to the wide number of commercial products using *Bacillus thuringiensis* (BT) strains, nuclear polyhedrosis viruses (NPV), granulosis viruses, microsporidians, nematodes, and fungi.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

I claim:

1. A method of treating vegetation comprising:
   (a) contacting the vegetation with a treating agent wherein the treating agent comprises a quinone and a microbial insecticide wherein the microbial insecticide comprises HzSNPV and wherein the weight ratio of quinone to microbial insecticide is less than about 50:1.

2. The method of claim 1 wherein the quinone is an ortho-quinone.

3. A method of treating vegetation comprising the steps of:
   (a) contacting a quinone and a microbial insecticide to form a treated microbial insecticide wherein the microbial insecticide comprises HzSNP and wherein the weight ratio of quinone to microbial insecticide is less than about 50:1 and (b) contacting the vegetation with the treated microbial insecticide.

4. The method of claim 3 wherein step (a) is carried out at a temperature in the range of 5° C. to 60° C., wherein the ratio of quinone to microbial insecticide is less than about 50:1, and wherein the contacting is carried out for a reaction time in the range of about 0.1 seconds to about 72 hours.

5. The method of claim 3 wherein step (a) is carried out at a temperature in the range of 15° C. to 35° C., wherein the ratio of quinone to microbial insecticide is less than about 10:1, and wherein the contacting is carried out for a reaction time in the range of about 0.1 seconds to about 10 hours.

6. The method of claim 3 wherein step (a) is carried out at a temperature in the range of 25° C. to 30° C., wherein the ratio of quinone to microbial insecticide is less than about 2:1, and wherein the contacting is carried out for a reaction time in the range of about 0.1 seconds to about 3 hours.

7. The method of claim 3 wherein the quinone is an ortho-quinone.

8. The method of claim 3 wherein the quinone is prepared by the oxidation of a phenolic.

9. The method of claim 3 wherein the quinone is prepared by the oxidation of phenolic wherein the phenolic is selected from a group comprising chlorgenic acid and dihydroxyphenylalanine.

10. The method of claim 9 where the phenolic is oxidized by an enzyme.

11. The method of claim 10 wherein the enzyme is selected from the group consisting of tyrosinase, laccase and peroxidase.

* * * * *